United States Patent [19]

Lelouch

[11] 4,070,102
[45] Jan. 24, 1978

[54] APPARATUS FOR SENSORY CONTROL OF A PERSON UNDERGOING TEST

[76] Inventor: Frederic Lelouch, 25 rue d'Estienne d'Orves, Vincennes 94300, France

[21] Appl. No.: 646,658

[22] Filed: Jan. 5, 1976

[30] Foreign Application Priority Data

Jan. 23, 1975 France .............................. 75 02066

[51] Int. Cl.² .......................... A61B 3/02; A61B 5/16
[52] U.S. Cl. ......................................... 351/18; 351/1; 351/17; 351/32; 351/36; 351/37; 273/1 E; 346/112
[58] Field of Search ....................... 351/17, 18, 30, 32, 351/36, 37, 1; 273/1 E; 346/139 R, 144, 68, 111, 112, 113

[56] References Cited

U.S. PATENT DOCUMENTS

| Re. 28,921 | 8/1976 | Haines et al. ...................... 351/36 X |
| 416,599 | 12/1889 | Green ................................. 351/18 X |
| 3,012,472 | 12/1961 | Feinberg et al. ....................... 351/36 |
| 3,288,546 | 11/1966 | Gans .................................... 351/36 X |
| 3,486,813 | 12/1969 | Johnston ............................ 351/36 X |
| 3,573,843 | 4/1971 | Solley ............................... 346/113 X |
| 3,698,385 | 10/1972 | Low et al. ........................ 273/1 E X |
| 3,747,589 | 7/1973 | Harrison et al. ................. 273/1 E X |
| 3,861,790 | 1/1975 | Tamura .............................. 351/36 X |
| 3,864,695 | 2/1975 | Nagashima et al. ............. 346/139 R |
| 3,905,688 | 9/1975 | Decker et al. ........................ 351/30 |

FOREIGN PATENT DOCUMENTS 2,315,686 10/1974 Germany .............................. 351/30

Primary Examiner—Paul A. Sacher
Assistant Examiner—John D. Lee
Attorney, Agent, or Firm—George B. Oujevolk

[57] ABSTRACT

A sensory control apparatus to determine the visual acuteness of persons tested. The apparatus has at least one optical device to view images of figures provided by a step-by-step parade means. The apparatus is operated by an electronic command module operated by a person tested when he has identified the images seen. Power feed means and display means to display the results are also provided. The device alerts the person tested of the start of ametropic vision and poor reflexes.

1 Claim, 10 Drawing Figures

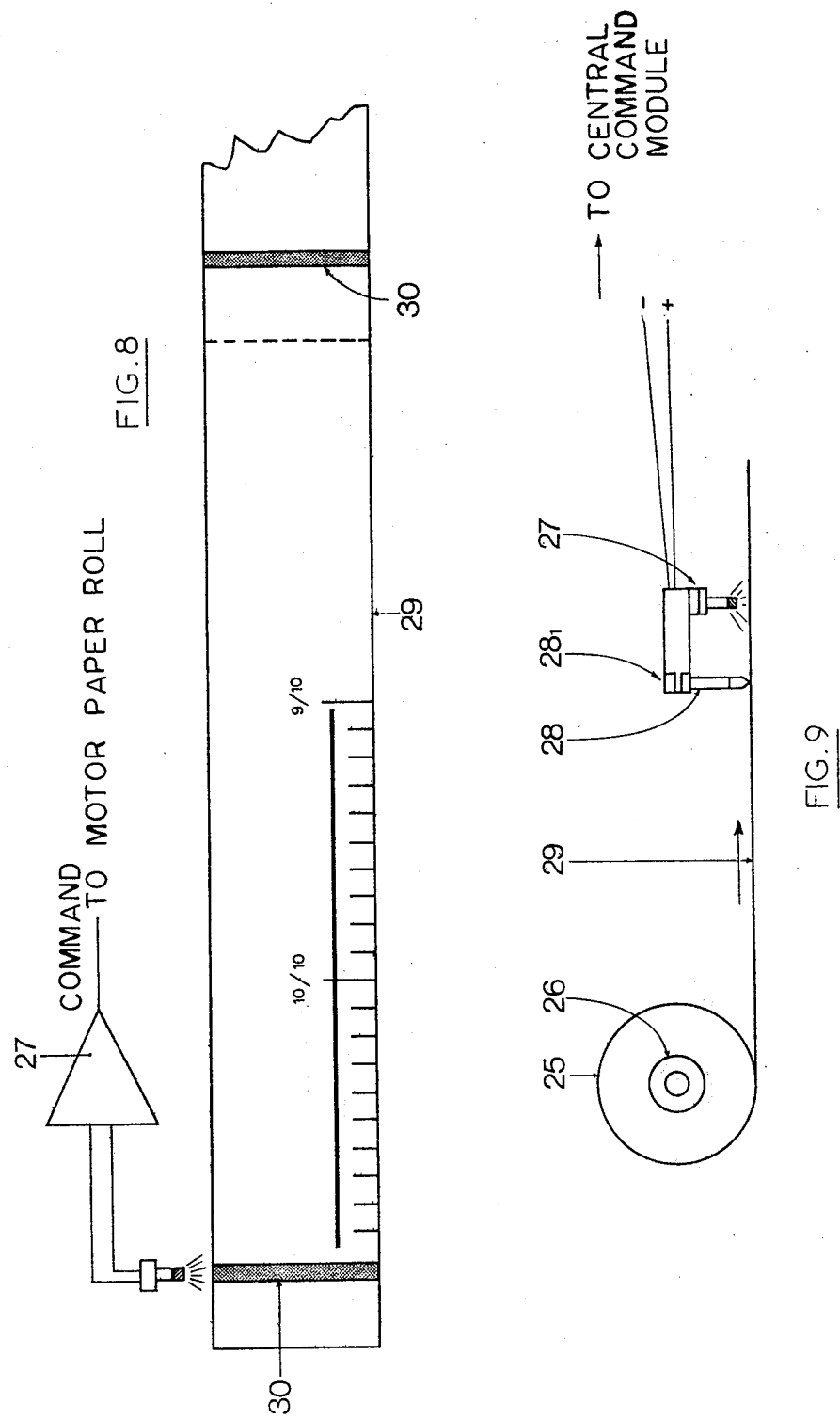

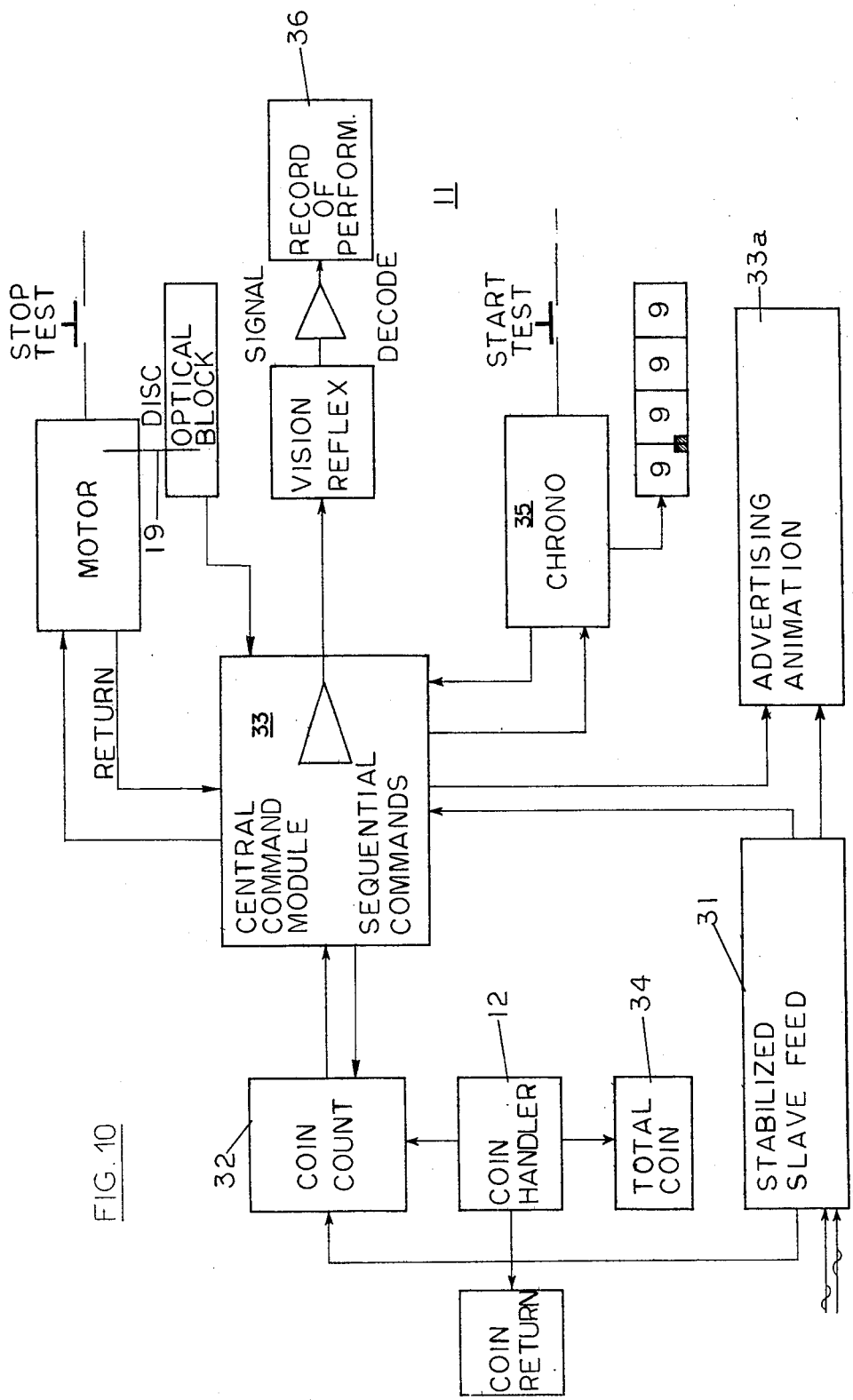

APPARATUS FOR SENSORY CONTROL OF A PERSON UNDERGOING TEST

BACKGROUND OF THE INVENTION

The present invention relates to sensory control testing and more particularly to a sensory control testing apparatus to determine the visual acuteness of human beings.

BRIEF DESCRIPTION OF THE PRIOR ART

With the present development of automobile traffic, it has become most important that drivers be informed exactly as to their vision and reflexes. The ignorance of these characteristics is a frequent cause of accidents. Unhappily, such ignorance is very widespread. This is due mainly to the fact that the sensory control of a person can only be tested by the intermediary of an expert who is not always on hand in a nearby area. The controls are therefore only established during visits to the physician, often widely spaced apart so that the person is not aware in time of the danger that he is to others and that he himself incurs.

Automobile traffic is only taken as an example; sensory control is very important for many other reasons, such as for professional reasons.

Furthermore, in the United States, many States have recently started to periodically retest drivers as to their vision and reflexes.

For the foregoing situation, an automatic apparatus, precise and easy to operate, where a physician or expert is not required, should be accessible to the public, or to the inspector of the motor vehicle bureau who tests the public. Such an apparatus is not on the market at the present time. We will examine hereafter the present state of the art in regard to the control of visual acuteness.

Visual acuteness is a simple criterion of ametropia, so that its measurement remains, up to the present time, the only subjective basis used in optometry. Thus, if $v$ is the minimum value of the visual angle which still permits the person tested to recognize an object ($v$ varying with the object selected for test purposes). The smaller the $v$, the better the vision and the greater the visual acuteness. If V is the visual acuteness, we have:

$$V = (\text{constant}/v)$$

The constant results from the particular units selected. The optometrical method used is a subjective method. This method is used by the opticians and, in general, by the non-professionals, so as to be devoid of any suspected practice of medecine. A method is subjective if the measuring instrument uses only the light which penetrates the person's eye, in which case the latter is the only judge of what is projected on his retina.

The method is objective insofar as the light diffused by the retina, outside of the eye, plays a part and, in such a case, an observer can make his measurements without the person tested having to make his own determination.

The two subjective methods used up to now are:
a. The Donders method
b. The subjective ophthalmometer a. Donder's method

The Donder's method is based on the determination by the person tested of the clarity of the images formed on his retina. For that purpose, test articles of small apparent diameter are presented to the subject and this technique thus corresponds to the equivalent of a visual acuteness examination.

Monoyer's scale

The tests used to determine the visual acuteness for nearly one century are of the printing types of various sizes. Capital letters are used and are called "optotypes."

It will be recalled that visual acuteness V is inversely proportional to the smallest visual angle $v$ under which the test is made at the limit of recognition. In the Monoyer test V is a fraction with a denominator of 10 (although in some countries a denominator of 20 is used) and of a numerator $m$, when the limit angle has a value in minutes: $v = 50/m$. In France, optotype scales are made to be seen at 5 meters, and the letters which correspond to $V = 10/10$ are 7.3 mm in height.

Monoyer's scale is composed of 10 lines of acuteness placed in arithmetical progression, each having a value of 1/10. For each degree of vision acuteness there is a corresponding specific height for each letter of the line, as indicated in the following table:

| Acuteness | 1 | 0.9 | 0.8 | 0.7 | 0.6 | 0.5 | 0.4 | 0.3 | 0.2 | 0.1 | |
|---|---|---|---|---|---|---|---|---|---|---|---|
| Corresponding height of optotype | 7.3 | 8.1 | 9.1 | 10.4 | 12.2 | 14.6 | 18.3 | 24.3 | 36.5 | 73 | mm |

Sometimes, instead of letters, a test called the Landolt broken ring test is used. This test appears to have less precision than the optotypes but is useful in areas where the population is generally illiterate. In this test the person tested must indicate the orientation of the break in the ring and this appears at the limit as the brighter part of the circle. Thus, for an equal dimension, the test is less precise than letters to the exactness of focusing. Besides, the assistance of a monitor is required.

In order to implement the Donder's method, the following are necessary:
1. a room of over 5 meters in length;
2. an optotype table disposed vertically at the eye's height;
3. a spacing of the figures at least equal to their width;
4. very black figures on a white background;
5. light or illumination obtained by diffusion transparency or by projection on a screen. It must be very uniform and must not vary by more than 10% from one section of the table to the other;
6. sufficient lighting, generally superior to the normal illumination of the room;
7. a monitor (optician, ophthalmologist, etc.); the visual acuteness of the person tested.

b. The subjective ophthalmometer

Under this name are classified various instruments which can be used by a subject or person tested to determine his own ametropia. The simplest and best known of these instruments is the Badal optometer.

Badal's optometer consists of a tube of a few centimeters in diameter, closed at one of its ends by a convex lens of a power of D (see FIG. 2). A second tube slides in the first one. It carries a small transparent test means, for example, a small photographic reproduction of an optotype table such as X The distance of the test means to the focal object of the lens F X' The distance between the test image and focal image F' of the lens f The focal length of the lens Newton's well known relationship is written as:

$$XX' = f^2$$

if the nearness (X' = 1/X') of the image in relation to the focal image is given as:

$$X' = -X/f^2 = X^{D2}$$

As an example: for $D = 15.8$ (diopters), a variation of 1 millimeter on X causes a variation of 0.25 dt on X'.

The advantage of this instrument over the Donder's method is that it is more convenient. In fact, it is a compact apparatus which the person can utilize by himself without the assistance of another.

The advantages and shortcomings of the two methods are:

The advantages of the Donder's method:
it is precise,
it is simple,
it is a method which in Monoyer scale, gives a measurement in simple fractions, easy to remember.

Disadvantages of the Donder's method
it requires a room 5 meters in length
it requires the presence of a monitor
the person tested must answer the questions of the monitor rational lighting Advantages of the subjective ophthalmometer
it is a compact apparatus
it is operated by the subject himself without having to answer questions of the monitor Disadvantages of the subjective ophthalmometer
the results are less precise than those obtained through the Donder's method
the person tested must look with one eye into the eye piece; this has the great inconvenience of being able to distract him so that he must concentrate and pay attention
the measurements are made in diopters which is a unit understood only by professionals. It is therefore necessary to obtain the services of a competent specialist to inform the person tested as to the condition of his vision.

The methods used for the control of reflexes are likewise complex and not very practical.

An object of this invention is to eliminate to a great extent the inconveniences of the known methods being in fact an apparatus for the sensory control of a person and has as an important feature the fact that it contains at least an optical device for the viewing of images and figures supplied by a device providing a sequential step by step parade of these figures, an electronic device comprising at least one control guide to be operated by the person after having succeeded in having identified the images viewed, a power source and a device to post the results of the control operation.

SUMMARY OF THE INVENTION

According to one embodiment, the optical instrument is provided with an eyepiece near the object-focus where is placed a support holding the figures to be viewed. This eyepiece giving a virtual image located at a given distance of the person's eye wherein at least one direction must be controlled, the eyepiece being located between the person and the spot provided for the person's eye, so that its focal image coincides with HELMHOLTZ'S point of the schematic ametropic eye, the figures being lighted by an electric bulb the position of which can be regulated by movement and which is fed by an energy producing device.

In another embodiment, the optical device has a translucent glass placed between the electrical bulb and the figures support, the support itself being held in position by the viewing screen and by a protective device, such as a transparent blade with parallel faces located between the eyepiece and the location of the persons eye.

In another embodiment, some figures intended to be viewed by the person in order to test his visual acuteness, are photographic reductions of one line of Monoyer's optotype table figures, the image of which are formed at five meters from the focal image of the eyepiece with an equal height at the level of the corresponding line of the optotype table, only one line of the table being shown in turn.

It is therefore seen that we utilize, in conformity with this invention, a photographic reduction of each line of the optotype table. These lines thus reduced (called stereotypes) are successively placed near the object focus of the eyepiece. This eyepiece is chosen so that it will give a virtual image of each stereotype, always located at 5 meters of the person's eye placed at the focal image of the eyepiece. The eyepiece is also chosen in such a way as to give an image of the stereotype having a height equal to that of the letters appearing on Monoyer's optotype table.

Thus, the image seen through the eyepiece is viewed by the person at the same angle α as the apparent angle under which he would observe the octotype table at 5 meters.

It therefore appears that the person, although using a subjective opthalmometer, is being submitted to Donder's method, since he himself reads, one by one, Monoyer's optotype table.

The apparatus contemplated by this invention allows the assembling of the two methods previously described while minimizing their disadvantages. It uses a subjective ophthalmometer based on the Donder's method.

In short:
the apparatus is compact;
it is automatic;
it does not in any way necessitate the presence of a monitor;
the apparatus is based on the Donder's method allowing the reading of optotype lines;
the results are shown in accordance with Monoyer's scale and are readily understandable;
at the same time the apparatus gives a timemeasure of the person's reflexes;
there is no written memo to be completed.

The apparatus has the further advantage as to reduce, as much as possible, the eye accommodation of the person because:

- the optotypes are presented line by line instead of the entire table;
- the time of presentation is limited so that the person is not under stress;
- the eye that does not observe stays open and looks at drawings chosen to further attenuate the accommodation phenomenom;
- the eyepiece is so conceived that its focal image coincides with Helmholtz's point, the retina image being thus free of accommodation.

The apparatus conforming to this invention allows, in a very simple way, to warn the person in regard to visual or reflex difficulties. It does not dispense with subsequent detailed examination by a qualified practitioner.

The invention will be better understood through the following description and by a study of the attached drawing showing one embodiment of the invention in which:

BRIEF DESCRIPTION OF THE DRAWINGS

FIG. 8 shows the registering device;

FIG. 9 is a corresponding cross section;

FIG. 10 is a drawing of the entire apparatus.

DETAILED DESCRIPTION

Figure 1:
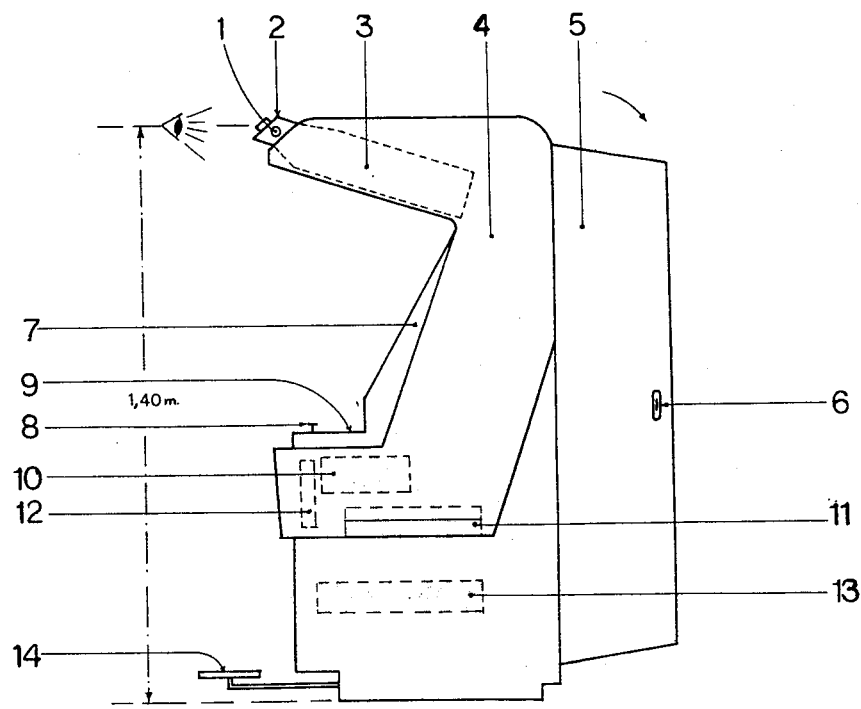
FIG. 1 is a lateral elevation of a sensory control apparatus in conformity with this invention.
Figure 2:
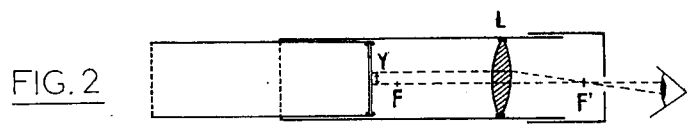
FIG. 2 is a view of a complete assembly of Badal's optometer.

As shown in FIG. 1, the apparatus for sensory control according to the inventive concept has a housing 4, an optical system 3, an electronic system 11, a register (or printer) 10, and a money receiving device 12.

The housing 4, made of synthetic matter, containing the apparatus mechanism, has a plate 9 on which are written the instructions concerning the operation. A rear door 5 provided with a lock 6 which gives access to the interior of the apparatus. An animated front 7 gives indications, especially as regards advertising.

Figure 3:
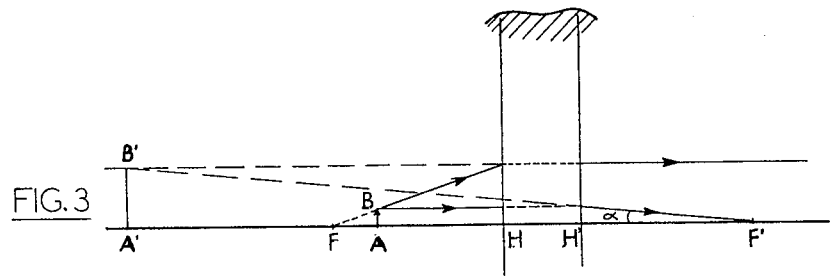
FIG. 3 is a schematic view of the eyepiece of the apparatus.

A slot, not shown, permits the introduction of coin pieces in the coin receiving device 12. These pieces are recovered in a cash drawer 13. The person may actuate a stop push button 8 during the visual acuteness test as well as a foot brake 14 during the reflex control test. Handles 1 may be gripped by the subject, for his convenience, during the control operations. The optical block has an eyepiece 2 shown with more detail on FIG. 3.

F and F' are the object and image focuses of the eyepiece;

H and H' are the principal planes;

A'B' is the image of the object AB;

The focal distances object and image are: $HF = H'F' = f$;

Thus, $HA = X$, the abcissa of the object type which originated at the object focus;

Thus, $H'F' = X'$, the abscissa of the image which originated at the image focus.

In accordance with Newton's well known formula $$XX' = FF' \qquad (1);$$

Since the eyepiece is bathed in air, we have:
$F = F'$ and the second Newton formula gives the magnification:

$$G = F/X = -X'/F' \qquad (2)$$

We have $X' = 5$ meters and if, for example, the eyepiece has a power $G = 10$, the formula (2) gives:

$$F = X'/G = 5/10 = 0.5 \text{ meter}.$$

Type positioning:

The relations (1) and (2) still allow us to determine the distance X of the object focus, at which the type must be located.

We obtain easily:

$$X = X'/G^2 \qquad (3);$$

Thus, in the case of the preceding example ($G = 10$);

$$X = 5/100 = 0.05 \text{ meter}.$$

In order to facilitate the technological selections the following table gives the value of X in relation to F and G:

| G | 7 | 10 | 20 | 25 | 30 | 50 | etc. |
|---|---|---|---|---|---|---|---|
| f in cm | 71 | 50 | 25 | 20 | 16.6 | 10 | |
| x n cm | 10 | 5 | 1.2 | 0.8 | 0.55 | 0.2 | |

It is evidently possible in view of the eyepieces available commercially to interpolate the preceding results.

Height of the type line:

The height of each line is evidently determined by its relation to the definition of magnification.

$h$ (type height) = H (image height)/G (magnification) $\qquad (4)$

The formula (4) gives for $G = 25$ the results shown in the following table:

| Acuteness | 1 | | 0.9 | | 0.1 | |
|---|---|---|---|---|---|---|
| Image height | 7.3 | | 8.1 | mm | 73 | mm |
| Stereotype height | 0.29 | | 0.32 | | 2.9 | mm |

Lighting

The luminance of the white background over which the optotypes are shown has a value of 10 lumens (10 candelas per m²). This value is chosen because it represents the point at which a normal man reaches a power of separation corresponding to the normal visual acuteness as defined by Donder's.

The luminance is obtained by the use of a bulb placed behind a translucent glass, in front of which the type is placed.

If L is the luminance we have:

$L = 10$ candelas/m²

The lighting E provided by the lamp is: $E = \pi L/P$

P is the albedo taken equal to 0.9

The lighting of the type must therefore be equal to $E = (3.14 \times 10) 0.9$ $E = 35$ watts/m²

Figure 4:
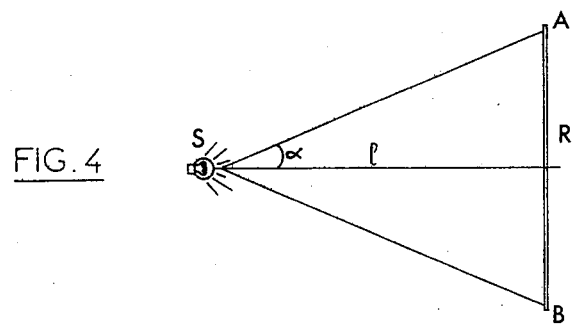
FIG. 4 is a drawing showing the location of the lamp in regard to the translucent glass in the apparatus.

Power of the bulb used (FIG. 4):

Given AB the translucent glass seen in a plane perpendicular to the plane of the paper.
Given R the ray of the translucent glass.
Given $l$ the distance from the bulb to the translucent glass.
Given $\alpha$ the half angle at the summit of the light cone by the lamps on the translucent glass.
Given I the intensity of the lamps.
Then the lighting E is given as:

$$E = \frac{2I(1 - \cos\alpha)}{R2} \text{ giving } I = \frac{ER2}{2(1 - \cos\alpha)}$$

If we take $\cos\alpha = \frac{1}{2}$ or an angle $\alpha$ of 30° and R = 2 cm, to obtain a lighting E of 35 watts/m2, the intensity of the lamp must be:

$$I = \frac{35 \times (0.02)^2}{2 \times \frac{1}{2}} = 35 \times 0.0004$$

whence I = 0.014 watts/steradian this corresponds approximately to a lamp having a power of: P = 175 milliwatts.

Figure 5:
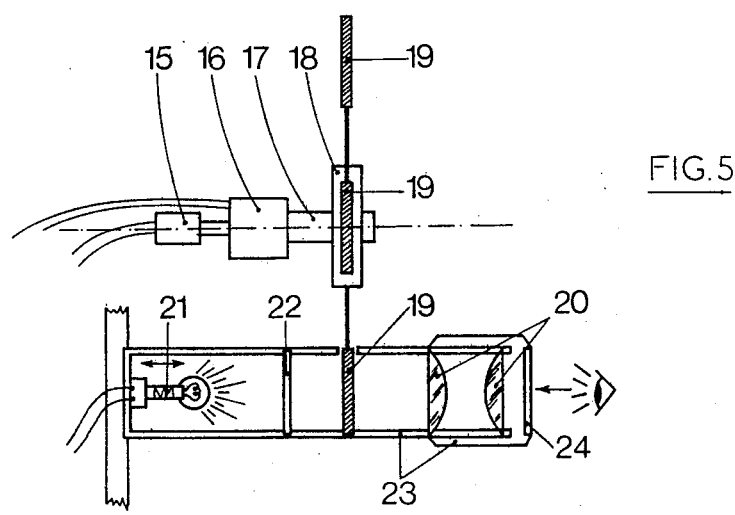
FIG. 5 is a side view of the optical section of the apparatus.

FIG. 5 represents the whole of the optical block. A motor 16, a potentiometer 15 as well as reducing means which support a rotating disc 18 of optotype 19. In that drawing the eyepiece is indicated as 20. It is used to examine the images of the optotypes shown on a background of translucent glass 22 lit by a lamp 21. A protective glass 24 is of a plate with parallel faces.

The stereotypes 19 are obtained by photoengraving or by photographic reduction.

As shown in FIG. 10, the electronic block 11 comprises:
A stabilizer feed arrangement 31;
coin counting means 32;
a central electronic command module 33 for the sequential performance of all operations as well as to service the lighting of the advertisement 33a;
a coin totalizer means 34;
a chronometer frequency meter 35;
a totalizer register 36 to record or display the results.

As must as possible of the foregoing are contained in a printed circuit.

Figure 6:
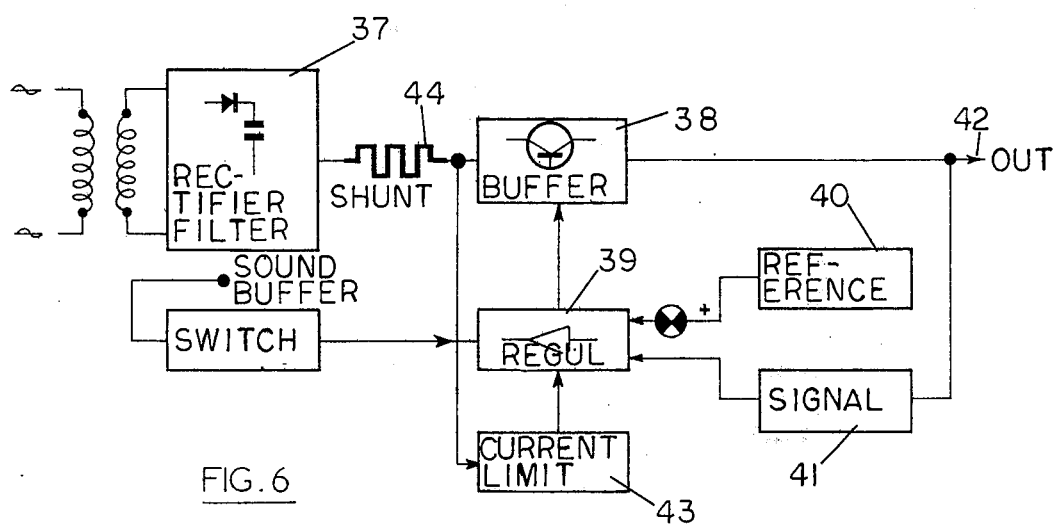
FIG. 6 shows the circuitry of the slave stabilized energy feeding system.

The operation of the slave stabilized feed circuit is well known (FIG. 6).

The voltage after passing through a rectifier filter is applied to a series buffer 38. This buffer is commanded by a regulator 39 which receives an error voltage signal obtained by taking the sum of a reference 40 and a voltage signal 41 taken from the output signal 42. If the current exceeds a preset limit, a current limit circuit 43 acts on the regulator. A shunt 44 supplies the circuit with a voltage proportional to the measured current.

The rectifier filter 37 consists of a diode bridge which rectifies the AC voltage supplied by the input transformer. A capacitor filters this voltage. The series mounted on a heat dissipator buffer consists of power transistors fed by a Darlington stage. The regulator 39 and current limit circuit 43 are integrated circuits.

The power is defined by the energy consumption of the apparatus. The electronic block includes the central command module 33 which controls the sequential functioning of the apparatus. Also, this central command module 33 provides the instructions which actuates the coin counter 32, the animated advertising 33a in front of the apparatus.

Finally, a portion of the central command module 33 is concerned with decoding and processing to provide the writing of the results, to advance the paper (not shown) and sense the position of the paper.

Figure 7:
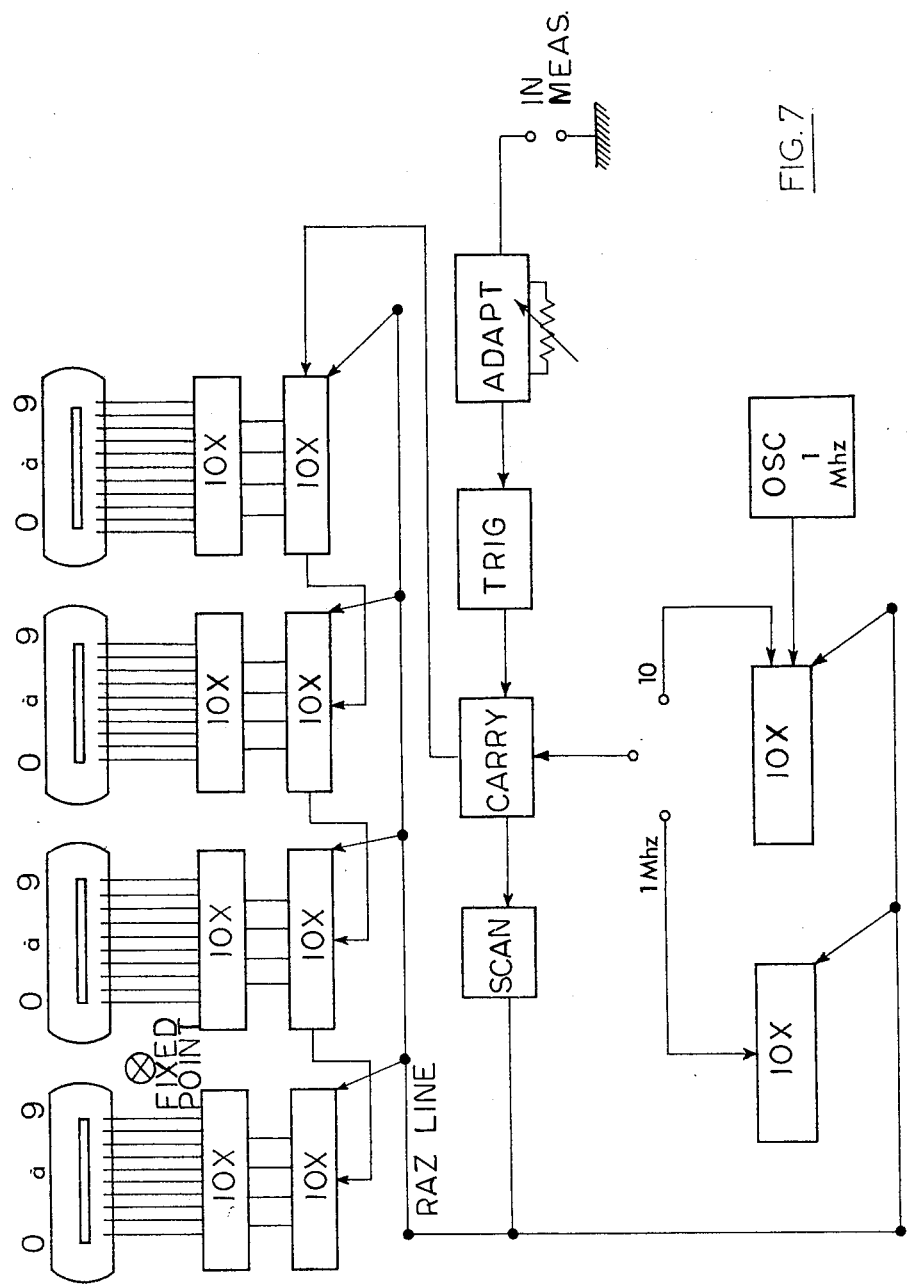
FIG. 7 shows the frequency metering system.

To control the reflexes the electronic block has a frequency meter regulated by a chronometer (FIG. 7). An electronic quartz apparatus or other timer of the prior art can be used. It is calibrated in a ten second interval (decade) full scale.

The central command module 33 gives a sound signal to start the chronometer 35. The counting by the chronometer will stop only when the person presses the brake pedal. This time period is determined by:
1. 4 tubes (nixies type) with a period after the first number so that the result will be:
   minimum . . . 0.001 second
   maximum . . . 9.999 seconds;
2. On the paper roll supplied to the person after the test, a table corresponding to time/realization is listed on the back of the paper roll.

The recorder or register of impressions (FIGS. 8 and 9) consists of a pre-printed band 25 actuated by a motor 26 which receives its starting command from the central order module 33. This central order module receives on its part the information of the paper positioning which is provided by the photo-optic system 27.

The system is very simple. Writing means 28 such as a fixed red pencil traces a line on the paper roll 29 which moves forward. This writing means is responsive to an electro-magnet $28_1$. The time of operation of the motor 26 (paper advance) is provided by the central command module, as a function of the results obtained from the person. The roll is automatically in the starting position of the first test, since the motor is stopped only upon detecting the block mark 30 preprinted on the roll (FIG. 8).

The recorder may be replaced on demand by an alpha numerical printer commercially available (Olympia-Sedelec, etc.).

The coin receiving device 12 is available commercially which operates with a 1 French franc piece (size about 25¢ U.S. currency). It can also accept coins of greater weight and diameter (example: Rejector national coin device or similar type). An electronic counter shows the person the number of remaining coins to be placed. Coins not conforming are rejected in a reject box provided for this pûrpose (see FIG. 10) and are not counted.

The apparatus operates as follows:
The person reads the instructions appearing on the plate of the apparatus. He introduces the first coin. A viewer indicates at each instant the number of coins which must still be introduced. The person continues to introduce coins required until the viewer shows zero (bad coins are rejected in the reject box and are not counted). When the viewer shows zero the apparatus is ready to carry out the control operation, the optical block lights up.

The first operation carried out consists in controlling the acuteness of the left eye. After a five second time period the first type is presented (acuteness 10/10). If the person can readily read the type he presses a pushbutton "stop" 8 located on plate 9. This push-button stops the running sequence. The person has six seconds to do this. If at the end of the time the person has not done this the next type appears (acuteness 9/10) and so on. When the sequence is stopped (by the "stop" button or the type runs out until 1/10) the central command module orders the recording or printing.

The type "passed to the right eye" is then presented. At the end of the lapse time of 10 seconds which serves as an installation and deconcentration the first type (acuteness 10/10) of the second test is presented. The sequence of operations then follows as in the first test.

After the second test is stopped or the type runs out at 1/10 there appears the type phrase "attention to the reflex test". The type phrase "Watch out for the stop" appears after a pause of four seconds.

The type "stop" is presented after a pause because of uncertain duration of 0 to six seconds to surprise the person. At the same time the electronic chronometer is started. The person then presses the "brake" pedal, the corresponding time is totalled and memorized. The central command module then gives a print or record command. The optical block light is extinguished and the paper roll comes out of the apparatus with the results of visual acuteness and reflex control which can be compared to ideal parameters printed on the back of the paper roll in graphics form. The paper roll is then positioned for a new departure and the apparatus is ready for the next test.

It is to be observed therefore that the maintenance of the apparatus is very simple. It can be placed at the disposal of a wide public. People who have a vision acuteness (7/10) or insufficient reflexes will certainly be urged to visit a specialist and will in any event be alerted. Thus, the apparatus does not enter into competition with medical circles since its objective is to direct the person to his physician in the case of the start of ametropic vision.

Of course, this invention is not limited to the embodiment herein described and other embodiments are possible without departing from the spirit of the invention.

The central command module described herein is known in the art and is shown in the Thomas A. Decker et al U.S. Pat. No. 3,905,688.

I claim:

1. In an instrument for testing sensory control to determine the visual acuteness as well as the reflexes of a person, said instrument having:
   a. a focusing optical instrument with a defined object focus;
   b. a figure image device with figures including step-by-step parade means, supplying a step-by-step laterally moveable parade of figure images to the optical instrument on a rotating disc having figure supports thereon, motor means coupled to the disc to rotate the disc and speed reducing means coupled between the disc and the motor;
   c. electronic means and a command module coupled to said optical instrument and said figure image device, operating means to operate the command module by the person tested including a coin box coupled to said command module having starter means responsive to start when provided with at least one coin and reject means to reject incorrect coins;
   d. an energy feeding device coupled to the command module and the figure image device; and,
   e. a result display device coupled to the command module to display the results of the test; in combination:
   f. an eyepiece in said optical instrument near the object focus at which location there is support means to hold the figures to be seen, said eyepiece providing vertical images situated at a predetermined distance from the eye of the person whose senses are to be tested, said eyepiece being located between said support and location of the eye of the person being tested, such that the image focus coincides with the Helmholtz point of the schematic ametropic eye, and light means to light up the figures laterally moveable, fed by said energy feeding devices;
   g. a frosted glass in said optical instrument disposed between the light means and the figure support, said support being mounted on the step-by-step parade means and a transparent blade-like protection means with parallel faces disposed between the eye-piece and the eye location of the person tested;
   h. a display recorder of the test structurally coupled to the command module having a pre-printed paper roll turned by a motor, said roll being divided into successive frames defined by black band transverse limit means cooperating with an electrical photocell to indicate the start of the frame to the command module, each frame having at least two zones graduated in a scale of 1/10 to 10/10, each corresponding to the visual acuteness of the person tested and writing means, actuated by an electromagnet to record the measurement of visual acuteness of the person tested when the command is given by the command module operated by the person, said writing means tracing a continuous curve on the face of the pre-printed paper roll as it unrolls, the interpretation of the curve opposite to one of the graduations of the roll defining the visual acuteness of the person tested; and,
   i. a frequency chronometer structurally coupled to the electronic command module so disposed as to measure the time lapse between the appearance of a given figure, designed to test the reflexes of the person tested and brake means coupled to the apparatus actuated by the person tested upon seeing said figure.

* * * * *